United States Patent [19]

Nelson et al.

[11] Patent Number: 5,385,909
[45] Date of Patent: Jan. 31, 1995

[54] HETEROCYCLIC ESTERS OF RAPAMYCIN

[75] Inventors: Frances C. Nelson; Guy A. Schiehser, both of Yardley, Pa.

[73] Assignee: American Home Products Corporation, Madison, N.J.

[21] Appl. No.: 156,208

[22] Filed: Nov. 22, 1993

[51] Int. Cl.[6] .................. A61K 31/495; C07D 487/04
[52] U.S. Cl. ...................................... 514/291; 540/456
[58] Field of Search .................. 540/456; 514/291

[56] References Cited

U.S. PATENT DOCUMENTS 3,929,992 12/1975 Sehgal et al. ..................... 424/122
3,993,749 11/1976 Sehgal et al. ..................... 424/122

(List continued on next page.)

FOREIGN PATENT DOCUMENTS 5075551A 7/1992 European Pat. Off. ............ 540/456

OTHER PUBLICATIONS

Kao et al., Commonly owned U.S. patent application Ser. No. 08/054,655, Filed: Apr. 23, 1993.
Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

Primary Examiner—Robert T. Bond
Attorney, Agent, or Firm—Arnold S. Milowsky

[57] ABSTRACT

A compound of the structure

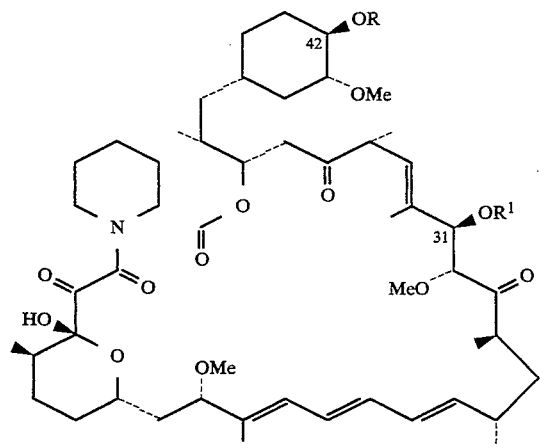

wherein R and $R^1$ are each, independently,

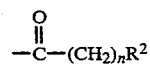

or hydrogen,
$R^2$ is a heterocyclic radical which may be optionally substituted;
n=0-6;

with the proviso that R and $R^1$ are both not hydrogen, or a pharmaceutically acceptable salt thereof which is useful as an immunosuppressive, antiinflammatory, antifungal, antiproliferative, and antitumor agent.

15 Claims, No Drawings

U.S. PATENT DOCUMENTS

| | | | |
|---|---|---|---|
| 4,316,885 | 2/1982 | Rakhit | 424/122 |
| 4,375,464 | 3/1993 | Sehgal et al. | 424/122 |
| 4,401,653 | 8/1983 | Eng | 424/122 |
| 4,650,803 | 3/1987 | Stella et al. | 514/291 |
| 4,885,171 | 12/1989 | Surendra et al. | 424/122 |
| 5,023,262 | 6/1991 | Caufield et al. | 514/291 |
| 5,023,263 | 6/1991 | Von Burg | 514/291 |
| 5,023,264 | 6/1991 | Caufield et al. | 514/291 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield | 514/183 |
| 5,118,677 | 6/1992 | Caufield | 514/183 |
| 5,118,678 | 6/1992 | Kao et al. | 514/183 |
| 5,120,842 | 6/1992 | Failli et al. | 540/542 |
| 5,130,307 | 7/1992 | Failli et al. | 514/321 |
| 5,138,051 | 8/1992 | Hughes et al. | 540/456 |
| 5,151,413 | 9/1992 | Caufield et al. | 514/63 |
| 5,169,851 | 12/1992 | Hughes et al. | 514/291 |
| 5,177,203 | 1/1993 | Failli et al. | 540/456 |
| 5,194,447 | 3/1993 | Kao | 514/542 |
| 5,221,670 | 6/1993 | Caufield | 514/183 |
| 5,233,036 | 8/1993 | Hughes | 540/455 |

HETEROCYCLIC ESTERS OF RAPAMYCIN

BACKGROUND OF THE INVENTION

This invention relates to heterocyclic esters of rapamycin and a method for using them for inducing immunosuppression, and in the treatment of transplantation rejection, graft vs. host disease, autoimmune diseases, diseases of inflammation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28,727 (1975); H. A. Baker et al., J. Antibiot. 31,539 (1978); U.S. Pat. Nos. 3,929,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1].

Mono- and diacylated derivatives of rapamycin (esterified at the 28 and 43 positions) have been shown to be useful as antifungal agents (U.S. Pat. No. 4,316,885) and used to make water soluble aminoacyl prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, antiinflammatory, antifungal, antiproliferative, and antitumor agents having the structure

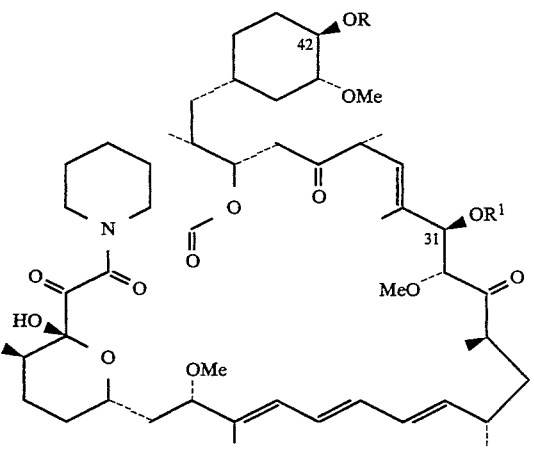

wherein R and $R^1$ are each, independently,

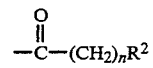

or hydrogen;

$R^2$ is a heterocyclic radical of 5-12 carbon atoms having at least one N, O, or S, which may be optionally mono-, di-, or tri-substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, trifluoromethoxy, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, $-SO_3H$, $-PO_3H$, and $-CO_2H$;

n=0-6;

with the proviso that R and $R^1$ are both not hydrogen, or a pharmaceutically acceptable salt thereof.

The pharmaceutically acceptable salts are those derived from such inorganic cations such as sodium, potassium, and the like; organic bases such as: mono-, di-, and trialkyl amines of 1-6 carbon atoms, per alkyl group and mono-, di-, and trihydroxyalkyl amines of 1-6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

It is preferred that the heterocyclic radical defined in $R^2$ be an unsaturated or partially saturated heterocyclic radical of 5-12 atoms having 1 ring or 2 fused rings. Preferred heterocyclic radicals include unsaturated heterocyclic radicals such as furanyl, thiophenyl, pyrrolyl, isopyrrolyl, pyrazolyl, imidazolyl, 1,2,3-triazolyl, 1,2,4-triazolyl, 1,2-dithiolyl, 1,3-dithiolyl, 1,2,3-oxathiolyl, isoxazolyl, oxazolyl, thiazolyl, isothiazolyl, 1,2,3-oxadiazolyl, 1,2,5-oxadiazolyl, 1,3,4-oxadiazolyl, 1,2,3,4-oxatriazolyl, 1,2,3,5-oxatriazolyl, 1,2,3-dioxazolyl, 1,2,4-dioxazolyl, 1,3,2-dioxazolyl, 1,3,4-dioxazolyl, 1,2,5-oxathiazolyl, 1,3-oxathiolyl, 1,2-pyranyl, 1,4-pyranyl, pyridinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,2,6-oxazinyl, 1,4-oxazinyl, isoxazinyl, 1,2,5-oxathiazinyl, 1,4-oxazinyl, o-isoxazinyl, p-isoxazinyl, 1,2,5-oxathiazinyl, 1,2,6-oxathiazinyl, 1,3,5,2-oxadiazinyl, azepinyl, oxepinyl, thiepinyl, 1,2,4-diazepinyl, benzofuranyl, isobenzofuranyl, thionaphthenyl, indolyl, indolenyl, 2-isobenzazolyl, 1,5-pyrindinyl, pyrano[3,4-b]pyrrolyl, benzpyrazolyl, benzisoxazolyl, benzoxazolyl, anthranilyl, 1,2-benzopyranyl, quinolinyl, isoquinolinyl, cinnolinyl, quinazolinyl, naphthyridinyl, pyrido[3,4-b]pyridinyl. pyrido[4,3-b]pyridinyl, pyrido[2,3-b]pyridinyl, 1,3,2-benzozazinyl, 1,4,2-benzoxazinyl, 2,3,1-benzoxazinyl, 3,1,4-benzoxazinyl, 1,2-benzisoxazinyl, 1,4-benzisoxazinyl, carbazolyl, purinyl, and partially saturated heterocyclic radicals selected from the list above. All of the preferred heterocyclic radicals contain at least one double bond. When the heterocyclic radical is partially saturated, one or more of the olefins in the unsaturated ring system is saturated; the partially saturated heterocyclic radical still contains at least one double bond. The —(CH$_2$)$_n$— sidechain can be attached to any position of the heterocyclic radical containing a carbon or nitrogen capable of forming a bond with the —(CH$_2$)$_n$— sidechain. More preferred heterocyclic radicals are pyridinyl, pyrazinyl, triazinyl, pyrimidinyl, pyridazinyl, imidazolyl, pyrazolyl, quinolinyl, tetrahydroquinolinyl, and isoquinolinyl.

It is preferred that the aryl moiety of the arylalkyl group is a phenyl, naphthyl, pyridinyl, quinolinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1o6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H. It is more preferred that the aryl moiety is a phenyl group that may be optionally substituted as described above. The term alkyl of 1–6 carbon atoms includes both straight chain as well as branched carbon chains.

Of the compounds of this invention, preferred members include those in which R$^1$ is hydrogen; those in which R$^1$ is hydrogen and n=0; and those in which R$^1$ is hydrogen, n=0; R$^2$ is pyridinyl, pyrazinyl, triazinyl, pyrimidinyl, pyridazinyl, imidazolyl, pyrazolyl, quinolinyl, tetrahydroquinolinyl, or isoquinolinyl.

Compounds which contain the ester group

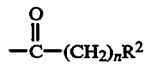

at the 42- or 31,42-positions can be prepared by converting an appropriately substituted heterocyclic or heterocyclicalkyl carboxylic acid to its mixed anhydride with an acylating group such as 2,4,6-trichlorobenzoyl chloride. Treatment of rapamycin with the mixed anhydride under mildly basic condition provides the desired compounds. Mixtures of 42- and 31,42-esters can be separated by chromatography. The starting heterocyclic or heterocyclicalkyl carboxylic acids are either commercially available or can be prepared by standard literature procedures.

The 31-esters of this invention can be prepared by protecting the 42-alcohol of rapamycin with a protecting group, such as with a tert-butyl dimethylsilyl group, followed by esterification of the 31-position by the procedures described above. The preparation of rapamycin 42-silyl ethers is described in U.S. Pat. No. B1 5,120,842, which is hereby incorporated by reference. Removal of the protecting group provides the 31-esterified compounds. In the case of the tert-butyl dimethylsilyl protecting group, deprotection can be accomplished under mildly acidic conditions, such as acetic acid/water/THF. The deprotection procedure is described in Example 15 of U.S. Pat. No. 5,118,678, which is hereby incorporated by reference.

Having the 31-position esterified and the 42-position deprotected, the 42-position can be esterified using a different acylating agent than was reacted with the 31-alcohol, to give compounds having different esters at the 31- and 42-positions. Alternatively, the 42-esterified compounds, prepared as described above, can be reacted with a different acylating agent to provide compounds having different esters at the 31- and 42-positions.

This invention also covers analogous hindered esters of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxyrapamycin [U.S. Pat. No. 5,102,876]. This invention also covers hindered esters at the 31-position of 42-oxorapamycin [U.S. Pat. No. 5,023,263]. The disclosures in the above cited U.S. Patents are hereby incorporated by reference.

Immunosuppressive activity for representative compounds of this invention was evaluated in an in vitro standard pharmacological test procedure to measure lymphocyte proliferation (LAF) and in three in vivo standard pharmacological test procedures. The pinch skin graft test procedure measures the immunosuppressive activity of the compound tested as well as the ability of the compound tested to inhibit or treat transplant rejection. The adjuvant arthritis standard pharmacological test procedure, which measures the ability of the compound tested to inhibit immune mediated inflammation. The adjuvant arthritis test procedure is a standard pharmacological test procedure for rheumatoid arthritis. Representative compounds of this invention were also evaluated in a heart allograft standard pharmacological test procedure which measures immunosuppressive activity of the compound tested as well as the ability of the compound tested to inhibit or treat transplant rejection. The procedures for these standard pharmacological test procedures are provided below.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An IC$_{50}$ was obtained for each test compound as well as for rapamycin. When evaluated as a comparator for the representative compounds of this invention, rapamycin had an IC$_{50}$ ranging from 0.5–1.9 nM. The results obtained are provided as an IC$_{50}$.

Representative compounds of this invention were also evaluated in an in vivo test procedure designed to determine the survival time of pinch skin graft from male BALB/c donors transplanted to male C$_3$H(H-2K) recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days±S.D.) of the drug treatment group was compared with the control group. The following table shows the results that were obtained. Results are expressed as the mean survival time in days. Untreated (control) pinch skin grafts are usually rejected within 6–7 days. Compounds were tested using a dose of 4 mg/kg.

The ability of the compounds of this invention to induce immunosuppression and inhibit or treat transplantation rejection was evaluated in a heterotropic heart allograft standard pharmacological test procedure that emulates transplantation rejection that occurs in humans. The following briefly describes the procedure that was used. Male BN rat neonate donors (less than 5 days of age) were humanely sacrificed, the thymus was dissected away from the heart. All connections with the thoracic cavity were severed and the heart was removed from the chest cavity and placed in cooled RPMI media where all adherent fat and fascia were removed. The heart was bisected in half, along the midline from the apex to the root of the aorta, to generate two approximately equal halves each containing atrial and ventricular tissue. Recipient male Lewis rats were anesthetized with phenobarbital (50 mg/mL; i.p.), the left inner ear was swabbed with povidine iodine, and 1 mL RPMI was injected subcutaneously above the cartilage plate to produce a fluid filled sac. A stab incision was made to the sac, into which was inserted a single half heart fragment. The pocket was sealed with a single drop of Vet-Seal (3M Animal Care Products). Recipients were divided into groups of 10 rats each. One group was untreated and the second group was treated with the compound to be treated was administered at a dosage of 300 μg/day following the transplantation procedure until graft failure occurred. Administration was i.p., either by manual injection or via an Azlet osmotic pump that was implanted into the peritoneum of the recipient rat. Grafts were inspected for loss of cardiac activity on day 7 post-transplant and subsequently on alternate days. Graft survival time is defined as the post-transplant day on which the heart graft has lost all contractile activity by visual inspection and/or cardiac monitor. Individual rejection times were averaged to produce a mean survival time for each treated group. Untreated heterotropic allografts are rejected in about 9–10 days.

The adjuvant arthritis standard pharmacological test procedure measures the ability of test compounds to prevent immune mediated inflammation and inhibit or treat rheumatoid arthritis. The following briefly describes the test procedure used. A group of rats (male inbread Wistar Lewis rats) are pre-treated with the compound to be tested (1 h prior to antigen) and then injected with Freud's Complete Adjuvant (FCA) in the right hind paw to induce arthritis. The rats are then orally dosed on a Monday, Wednesday, Friday schedule from day 0–14 for a total of 7 doses. Both hind paws are measured on days 16, 23, and 30. The difference in paw volume (mL) from day 16 to day 0 is determined and a percent change from control is obtained. The left hind paw (uninjected paw) inflammation is caused by T-cell mediated inflammation and is recorded in the above table (% change from control). The right hind paw inflammation, on the other hand, is caused by non-specific inflammation. Compounds were tested at a dose of 2 mg/kg. The results are expressed as the percent change in the uninjected paw at day 16 versus control; the more negative the percent change, the more potent the compound. Rapamycin provided between −70% and −90% change versus control, indicating that rapamycin treated rats had between 70–90% less immune induced inflammation than control rats.

The results obtained in these standard pharmacological test procedures are provided following the procedure for making the specific compound that was tested.

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. Further demonstration of the utility of the compounds of this invention as immunosuppressive agents was shown by the results obtained in the skin graft, adjuvant arthritis, and heart allograft standard pharmacological test procedures. Additionally, the results obtained in the skin graft and heart allograft test procedures further demonstrates the ability of the compounds of this invention to treat or inhibit transplantation rejection. The results obtained in the adjuvant arthritis standard pharmacological test procedure further demonstrate the ability of the compounds of this invention to treat or inhibit rheumatoid arthritis.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

Because of the activity profile obtained, the compounds of this invention also are considered to have antitumor, antifungal activities, and antiproliferative activities. The compounds of this invention therefore also useful in treating solid tumors, adult T-cell leukemia/lymphoma, fungal infections, and hyperproliferative vascular diseases such as restenosis and atherosclerosis.

When administered for the treatment or inhibition of the above disease states, the compounds of this invention can be administered to a mammal orally, parenterally, intranasally, intrabronchially, transdermally, topically, intravaginally, or rectally.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention can be formulated neat or with a pharmaceutical carder to a mammal in need thereof. The pharmaceutical carrier may be solid or liquid. When formulated orally, it has been found that 0.01% Tween 80 in PHOSAL PC-50 (phospholipid concentrate with 1,2-propylene glycol, A. Nattermann & Cie. GmbH) provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carder, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 $\mu$g/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation and biological activities of representative compounds of this invention.

EXAMPLE 1

Rapamycin 42-ester with 2-methylnicotinic acid

To ethyl-2-methyl nicotinate (3 g, 18.1 mmol) in 15 mL of a 4:4:1 THF:MeOH:H$_2$O solution was added LiOH•H$_2$O (1.14 g, 27.3 mmol). The reaction was stirred overnight and then quenched with 2.2 mL of concentrated HCl. The resulting solid was collected and dried under high vacuum to afford 2-methylnicotinic acid in quantitative yield.

$^1$H NMR (300 MHz, DMSO) δ2.65 (s, 3H), 7.3 (m, 1H), 8.1 (m, 1H), 8.6 (m, 1H), 13.1 (br, s, 1H).

2-Methylnicotinic acid (0.3 g, 2.2 mmol) was dissolved in THF (14 mL). Triethylamine (0.37 mL, 2.64 mmol) was added and the solution was cooled to 0° C. Trichlorobenzoyl chloride (0.34 mL, 2.2 mmol) was added dropwise. The reaction was held at 0° C. for an additional 30 min and then allowed to warm to room temperature and stir for 3 h. The THF was evaporated via a stream of N$_2$ and benzene (7 mL) was added. Rapamycin (2 g, 2.2 mmol) was added followed by dimethylaminopyridine (DMAP) (0.32 g, 2.64 mmol). The resulting suspension was stirred overnight and then quenched with NaHCO$_3$ and diluted with ethyl acetate. The organic phase was washed with 0.1N HCl, NaHCO$_3$, brine, dried over Na$_2$SO$_4$, concentrated and chromatographed using 95/5 methylene chloride/isopropanol to give the title compound in 38% yield. mp=109°–113° C.

IR(KBr) 980 (w), 1075 (w), 1240 (w), 1440 (m), 1640 (m), 1725 (s), 2900 (s), 3400 (s, br); $^1$H NMR (400 MHz, CDCl$_3$) δ0.83 (m, 1H), 0.94 (m, 6H), 0.99 (d, J=6.5 Hz, 3H), 1.06 (d, J=6.6 Hz, 3H), 1.10 (d, J=6.7 Hz, 3H), 1.15–1.28 (comp m, 8H), 1.43–1.52 (comp m, 6H), 1.60 (m, 2H), 1.65 (s, 3H), 1.70 (s, 3H), 1.76 (d, 5=1.0, 3H), 1.79 (m, 2H), 1.99 (m, 1H), 2.17 (m, 3H), 2.35 (m, 2H), 2.61 (m, 1H), 2.73 (dd, J =5.7, 16.7 Hz, 2H), 2.84 (s, 3H), 3.14 (s, 3H), 3.34 (m, 2H), 3.34 (s, superimp on m, 3H), 3.38 (s, 3H), 3.57 (d, s=13.5, 1H), 3.67 (m, 1H), 3.74 (d, J=5.8 Hz, 1H), 3.90 (m, 1H), 4.19 (d, J=6.3, 1H), 4.79 (s, 1H), 4.90 (m, 1H), 5.19 (m, 1H), 5.29 (d, J=4.9 Hz, 1H), 5.42 (d, J=9.9 Hz, 1H), 5.55 (dd, J=8.8, 15.1 Hz, 1H), 5.97 (d, J=10.7 Hz, 1H), 6.15 (dd, J=9.9, 14.9 Hz, 1H), 6.36 (m, 2H), 7.22 (dd, J=4.8, 7.8, Hz 1H), 8.16 (dd, J=1.8, 7.9 Hz, 1H), 8.60 (dd, J=1.8, 4.8, Hz 1H); $^{13}$C NMR (100 MHz, CDCl$_3$) δ5 10.2, 13.2, 13.7, 15.9, 16.0, 16.1, 16.2, 20.7, 21.5, 24.7, 25.3, 27.0, 27.2, 29.8, 31.3, 32.8, 32.9, 33.2, 33.7, 35.1, 35.8, 38.4, 38.9, 40.2, 40.5, 41.5, 44.2, 48.0, 51.3, 55.9, 57.2, 59.3, 67.2, 75.4, 76.9, 77.2, 81.0, 84.3, 84.7, 98.5, 120.8, 126.4, 126.6, 129.5, 130.2, 133.6, 135.6, 136.0, 138.2, 140.1, 151.6, 159.6, 166.3, 166.7, 169.2, 192.5,208.2, 215.4; high resolution mass spectrum (negative ion FAB) m/z 1033.3 [(M-•); calcd for C$_{58}$H$_{84}$N$_2$O$_{14}$: 1032.7].

Results obtained in standard pharmacological test procedures:

LAF IC$_{50}$:1.00 nM

Skin graft survival: 11.2±0.8 days

Percent change in adjuvant arthritis versus control: −88%

Heart allograft survival: 29.9 days, i.p.

EXAMPLE 2

Rapamycin 42-ester with nicotinic acid

The title compound was prepared from nicotinic acid according to the procedure of Example 1. Purification was accomplished by HPLC (C18 reverse phase) using 20% acetonitrile in H$_2$O (0.1% acetic acid)-100% acetonitrile over 1 h to provide the title compound in 16% yield. mp=95°–98° C.

IR(KBr): 700 (w), 740 (w), 990 (m), 1020 (w), 1100 (m), 1200 (2), 1240 (w), 1285 (m), 1325 (w), 1375 (w), 1450 (m), 1590 (w), 1645 (s), 1720 (s), 2950 (s), 3440 (b); $^1$H NMR (400 MHz, CDCl$_3$) δ0.92 (d, J=7.47 Hz, 3H), 0.93 (d, J=6.85 Hz, 3H), 0.97 (d, J=6.43 Hz, 3H), 1.04 (d, J=6.64 Hz, 3H), 1.09 (d, J=6.64 Hz, 3H), 1.64 (s, 3H), 1.74 (s, 3H), 1.74 (s, 3H), 0.95–1.95 (comp m, 19H), 1.97 (comp m, 4H), 2.13 (m, 2H), 2.31 (m, 3H), 2.60 (d, J=6.43 Hz, 1H), 2.71 (m, 2H), 3.12 (s, 3H), 3.32 (s, 3H), 3.38 (s, 3H), 3.65–3.35 (m, 4H), 3.71 (d, J=6.02 Hz, 1H), 3.83 (m, 1H), 4.17 (d, J=6.23 Hz, 1H), 4.78 (s, exchangeable, 1H), 4.92 (m, 1H), 5.17 (m, 1H), 5.27 (m, 1H), 5.41 (d, J=9.96 Hz, 1H), 5.50 (m, 1H), 5.95 (d, J=10.38 Hz, 1H), 6.13 (m, 1H), 6.34 (comp m, 2H), 7.38 (m, 1H), 8.29 (m, 1H), 8.75 (m, 1H), 9.21 (m, 1H); high resolution mass spectrum (negative ion FAB) m/z 1018.1 [(M-•); calcd for C$_{57}$H$_{82}$N$_2$O$_{14}$: 1018].

Results obtained in standard pharmacological test procedures:

LAF IC$_{50}$: 0.17 nM

Skin graft survival: 9.60±0.89 days

EXAMPLE 3

Rapamycin 42-ester with 6-methylpyridine-3-carboxylic acid

The title compound was prepared from 6-methylpyridine-3-carboxylic acid according to the procedure of Example 1. Purification was accomplished using 5% methanol in methylene chloride followed by HPLC (C18 reverse phase) using 20% acetonitrile in H$_2$O (0.1% acetonitrile)-100% acetonitrile over 1 h to give the title compound in 12% yield. mp=109°–112° C.

IR(KBr) 730 (w), 760 (w), 910 (w), 990 (m), 1020 (w), 1100 (b), 1190 (w), 1280 (m), 1320 (w), 1380 (w), 1450 (m), 1600 (w), 1645 (m), 1720 (s), 2940 (s), 3430 (b); $^1$H NMR (400 MHz CDCl$_3$) δ0.91 (d, J=6.85 Hz, 3H), 0.93 (d, J=6.64 Hz, 3H), 0.98 (d, J=6.64 Hz, 3H), 1.04 (d, J=6.64 Hz, 3H), 1.09 (d, J=6.84 Hz, 3H), 1.64 (s, 3H), 1.74 (s, 3H), 0.81–1.95 (m, complex, 17H), 1.96 (m, 4H), 2.12 (m, 2H), 2.31 (m, 3H), 2.59 (m, 1H), 2.61 (s, 3H), 2.71 (m, 2H), 2.84 (m, 1H), 3.10–3.41 (comp m, 2H), 3.13 (s, 3H), 3.32 (s, 3H), 3.38 (s, 3H), 3.42 (m, 1H), 3.56 (m, 1H), 3.65 (m, 1H), 3.71 (d, J=6.02 Hz, 1H), 3.86 (m, 1H), 4.16 (m, 1H), 4.78 (s, 1H exchangeable), 4.91 (m, 1H), 5.17 (m, 1H), 5.28 (m, 1H), 5.41 (d, J=8.72 Hz, 1H), 5.54 (m, 1H), 5.95 (d, J=9.34 Hz, 1H), 6.13 (m, 1H), 6.33 (m, 2H), 7.22 (m, 1H), 8.16 (m, 1H), 9.08 (m, 1H); high resolution mass spectrum (negative ion FAB) m/z 1032.4 [(M-•); calcd for C$_{58}$H$_{84}$N$_2$O$_{14}$: 1032].

Results obtained in standard pharmacological test procedures:

LAF IC$_{50}$: 0.6 nM

Skin graft survival: 12.5±0.58 days

Percent change in adjuvant arthritis versus control: −87%

EXAMPLE 4

Rapamycin 42-ester with 5-methylpyrazine-2-carboxylic acid

The title compound was prepared from 5-methylpyrazine-2-carboxylic acid according to the procedure of Example 1. Purification was accomplished by chromatography with 2% methanol in methylene chloride to give the title compound in 12% yield. mp 115°–119° C.

IR(KBr) 730(w), 790 (w), 870 (w), 990 (m), 1030 (w), 1100 (w), 1140 (w), 1240 (w), 1280 (m), 1325 (w), 1375 (m), 1455 (m), 1650 (s), 1720 (s), 2930 (s), 3430 (b); $^1$H NMR (400 MHz CDCl$_3$) δ0.91 (d, J=6.85 Hz, 3H), 0.94 (d, J=6.64 Hz, 3H), 0.98 (d, J=6.43 Hz, 3H), 1.04 (d, J=6.43 Hz, 3H), 1.09 (d, J=6.71 Hz, 3H), 1.63 (s, 3H), 1.74 (s, 3H), 0.95-1.95 (comp m, 19H), 1.96 (comp m 4H), 2.15 (m, 2H), 2.31 (m, 2H), 2.61 (m, 2H), 2.65 (s, 3H), 2.71 (m, 1H), 3.10–3.36 (comp m, 2H), 3.12 (s, 3H), 3.32 (s, 3H), 3.38 (s, 3H), 3.40 (m, 1H), 3.55 (m, 1H), 3.65 (m, 1H), 3.71 (d, J=5.81 Hz, 1H), 3.81 (m, 1H), 4.17 (d, J=6.23 Hz, 1H), 4.77 (s, exchangeable, 1H), 5.02 (m, 1H), 5.16 (m, 1H), 5.23 (m, 1H), 5.41 (d, J=9.96 Hz, 1H), 5.52 (m, 1H), 5.93 (d, J=9.75 Hz, 1H), 6.13 (dd, J=9.86, 15.05 Hz, 1H), 6.33 (m, 2H ), 8.57 (s, 1H), 9.17 (s, 1H); $^{13}$C NMR (100 MHz, CDCl$_3$) δ10.15, 13.14, 13.78, 15.97, 16.07, 16.22, 20.66, 21.53, 21.91, 25.28, 27.04, 27.25, 29.70, 31.26, 31.38, 32.94, 33.73, 35.11, 35.94, 38.26, 38.86, 40.20, 40.73, 41.43, 44.21, 46.58, 51.27, 55.86, 57.60, 59.34, 67.18, 75.56, 77.15, 78.00, 80.72, 80.77, 84.36, 84.88, 98.49, 126.36, 126.64, 129.60, 130.13, 133.66, 135.50, 136.07, 140.22, 140.94, 144.27, 145.40, 157.55, 163.73, 166.77, 169.23, 192.51, 208.19, 215.49; high resolution mass spectrum (negative ion FAB) m/z 1033 [(M-•); calcd for C$_{57}$H$_{83}$N$_3$O$_{14}$: 1033].

Results obtained in standard pharmacological test procedures:

LAF IC$_{50}$: 0.28 nM

Skin graft survival: 11.33±0.82 days

Percent change in adjuvant arthritis versus control: −90%

EXAMPLE 5

Rapamycin 42-ester with quinoline 8-carboxylic acid

The title compound was prepared from 5-methylpyrazine-2-carboxylic acid according to the procedure of Example 1. Purification was accomplished by chromatography with 50–100% ethyl acetate in hexane followed by recrystallization from cyclohexane to give the title compound in 17% yield. mp=116°–119° C.

IR(KBr) 985 (w), 1195 (m), 1275 (m), 1450 (s), 1645 (s), 1720 (s), 2920 (s), 3420 (s); $^1$H NMR (400 MHz CDCl$_3$) δ0.83 (m, 1H), 0.91 (d, J=6.8 Hz, 3H), 0.93 (d, J=6.6 Hz, 3H), 0.97 (d, J=6.4 Hz, 3H), 1.04 (d, J=6.6 Hz, 3H), 1.09 (d, J=6.8 Hz, 3H), 1.40–1.55 (comp m, 10H), 1.58 (s, superimp on comp m, 3H), 1.73 (d, superimp on comp m, J=0.4 Hz, 3H), 1.70–1.90 (comp m, 12H), 1.98 (m, 2H), 2.15 (m, 1H), 2.34 (m, 2H), 2.59 (m, 1H), 2.72 (m, 2H), 3.12 (s, 3H), 3.32 (s, 3H), 3.30–3.43 (comp m, 2H), 3.44 (s, 3H), 3.55 (m, 1H), 3.65 (m, 1H), 3.71 (d, J=5.8 Hz, 1H), 3.80 (m, 1H), 4.17 (d, J=0.4 Hz, 1H), 4.79 (d, J=0.6 Hz, 1H), 5.05 (m, 1H), 5.19 (m, 1H), 5.35 (m, 1H), 5.42 (d, J=10 Hz, 1H), 5.59 (m, 1H), 5.97 (d, J=0.6 Hz, 1H), 6.14 (m, 1H), 6.33 (m, 2H), 7.43 (dd, J=4.2, 8.6 Hz, 1H), 7.55 (m, 1H), 7.92 (dd, J=1.3, 8.3 Hz, 1H), 7.98 (dd, J=1.45, 7.1 Hz, 1H), 8.16 (dd, J=1.6, 8.5 Hz, 1H), 9.01 (dd, J=1.86, 4.3 Hz, 1H); high resolution mass spectrum (negative ion FAB) m/z 1068.6 [(M-•); calcd for C$_{61}$H$_{84}$N$_2$O$_{14}$: 1068.6]. Anal. Calcd for C$_{61}$H$_{84}$N$_2$O$_{14}$: C, 68.52; H, 7.92; N, 2.62. Found: C, 68.77; H, 7.90; N, 3.11.

EXAMPLE 6

Rapamycin 42-ester with quinoline-6-carboxylic acid

The title compound was prepared from quinoline 8-carboxylic acid according to the procedure of Example 1. Purification was accomplished by chromatography with 50–100% ethyl acetate in hexane followed by recrystallization from cyclohexane to give the title compound in 11% yield. mp=115°–118° C.

IR(KBr) 965 (w), 1070 (w), 1170 (w), 1260 (w), 1440 (m), 1625 (m), 1710 (s), 2910 (s), 3440 (s, br); $^1$H NMR (400 MHz CDCl$_3$) δ0.85 (m, 1H), 0.92 (d, J=4.6 Hz, 3H), 0.94 (d, J=4.6 Hz, 3H), 0.98 (d, J=6.6 Hz, 3H), 1.04 (d, J=6.4 Hz, 3H), 1.09 (d, J=6.8 Hz, 3H), 1.15–1.60 (comp m, 14H), 1.64 (d, J=0.83 Hz, 3H), 1.75 (m, 6H), 1.75 (d, superimp on m, J=1.03 Hz, 3H), 2.00 (m, 2H), 2.19 (m, 3H), 2.30 (m, 2H), 2.59 (m, 1H), 2.70 (m, 2H), 3.12 (s, 3H), 3.32 (s, 3H), 3.41 (s, 3H), 3.42 (m, 2H), 3.55 (d, J=10 Hz, 1H), 3.72 (d, J=5.0 Hz, 1H), 3.38 (m, 1H), 4.18 (d, J=6 Hz, 1H), 4.76 (s, 1H), 5.00 (m, I H), 5.20 (m, 1H), 5.27 (d, J=0.6 Hz, 1H), 5.42 (d, J=10 Hz, 1H), 5.55 (m, 1H), 5.95 (J=8.0 Hz, 1H), 6.10 (m, 1H), 6.30 (m, 2H), 7.46 (q, J=4.0 Hz, 1H), 8.14 (d, J=9.0 Hz, 1H), 8.28 (m, 2H), 8.58 (m, 1H), 9.00 (m, 1H); high resolution mass spectrum (negative ion FAB) m/z 1068.6 [(M-•); calcd for C$_{61}$H$_{84}$N$_2$O$_{14}$: 1068.6]. Anal. Calcd for C$_{61}$H$_{84}$N$_2$O$_{14}$±0.2 C$_6$H$_{12}$: C, 67.45; H, 7.79; N, 2.57. Found: C, 67.61; H, 7.86; N, 2.40.

EXAMPLE 7

Rapamycin 42-ester with 1-methyl-1,2,3,4-tetrahydroquinoline-6-carboxylic acid

Quinoline-6-carboxylic acid (1.0 eq, 14.01 mmol) and ammonium formate (22 g, 350.1 mmol) were dissolved in MeOH (100 mL) and 10% Pd/C (4.04 g) was added. The solution was heated at reflux for 2.5 h then cooled to room temperature and filtered through celite. The solvent was removed to provide 1,2,3,4-tetrahydroquinoline-6-carboxylic acid in quantitative yield. $^1$H NMR (200 MHz, DMSO) δ1.78 (m, 2H), 2.65 ((m, 2H), 3.2 (m, 2H), 6.4 (m, 2H), 7.45 (m, 2H).

1,2,3,4-Tetrahydroquinoline-6-carboxylic acid (2.49 g, 1.0 eq) was dissolved in EtOH (200mL). 30% Formaldehyde (4 mL) and 10% Pd/C (2.0 g) were added. The reaction was hydrogenated at 50 psi overnight. The catalyst was filtered off and the solvent evaporated to provide crude 1-methyl-1,2,3,4-tetrahydroquinoline-6-carboxylic acid which was purified via flash column chromatography using hexane/ethyl acetate 50/50–100% ethyl acetate to provide 1.44 g (54%) of the desired product. $^1$H NMR (200 MHz, DMSO) δ1.89 (m, 2H), 2.71 (t, 2H), 2.9 (s, 2H), 3.3 (t, 2H), 6.52 (d, 1H), 7.46 (s, 1H), 7.6 (dd, 1H).

The title compound was prepared from 1-methyl-1,2,3,4-tetrahydroquinoline-6-carboxylic acid according to the procedure of Example 1. Purification was accomplished by flash chromatography using 5% methanol in methylene chloride followed by HPLC (C18 reverse phase) using 20% acetonitrile in H$_2$O (0.1% acetonitrile)-100% acetonitrile over 1 h to give the title compound in 9%. mp=124°–127° C.

IR (KBr) 860 (w), 985 (w), 1100 (w), 1190 (w), 1200 (w), 1280 (m), 1320 (m), 1440 (m), 1520 9m), 1605 (s), 1650 (m), 1710 (s), 2930 (s), 3420 (s, br); $^1$H NMR (400 MHz CDCl$_3$) δ8 0.92 (d, J=6.64 Hz, 3H), 0.95 (d, J=6.64 Hz, 3H), 0.99 (d, J=6.44 Hz, 3H), 1.06 (d, J=6.64 Hz, 3H), 1.11 (d, J=6.83 Hz, 3H), 1.61 (s, 3H), 1.75 (s, 3H), 0.81–1.95 (comp m, 19H), 1.96 (m, 4H), 1.99 (m, 2H), 2.12 (m, 2H), 2.34 (m, 3H), 2.60 (m, 1H), 2.76 (m, 3H), 2.96 (s, 3H), 3.14 (s, 3H), 3.34 (s, 3H), 3.42 (s, 3H), 3.10–3.41 (comp m, 2H), 3.56 (m, 1H), 3.66 (m, 1H), 3.74 (d, J=5.86 Hz, 1H), 3.81 (m, 1H), 4.20 (d, J=6.25 Hz, 1 H), 4.80 (s, 1H), 4.87 (m, 1H), 5.18 (m, 1H), 5.28 (m, 1H), 5.43 (d, J=10.1 Hz, 1H), 5.56 (m, 1H), 5.97 (d, J=9.7 Hz, 1H), 6.14 (m, 1H), 6.34 (m, 2H), 6.51 (d, J=8.79 Hz, 1H), 7.62 (m, 1H), 7.76 (m, 1H); $^{13}$C NMR (100 MHz, CDCl$_3$) δ10.10, 13.16, 13.61, 15.92, 16.06, 16.21, 20.63, 21.44, 21.81, 25.26, 27.01, 27.20, 27.70, 30.01, 31.22, 31.38, 33.01, 33.27, 33.68, 35.02, 38.31, 38.70, 38.83, 40.15, 40.73, 41.44, 44.19, 46.57, 51.06, 51.22, 55.86, 58.18, 59.26, 67.13, 75.52, 76.10, 77.10, 81.21, 84.31, 84.76, 98.45, 109.16, 116.94, 121.37, 126.36, 126.57, 129.58, 129.63, 130.12, 130.17, 133.64, 135.50, 135.99, 140.15, 149.88, 166.51, 166.76, 169.23, 192.52, 208.29, 215.46; high resolution mass spectrum (negative ion FAB) m/z 1086.8 [(M-•); calcd for $C_{62}H_{90}N_2O_{14}$: 1086.8].

What is claimed is:

1. A compound of the structure

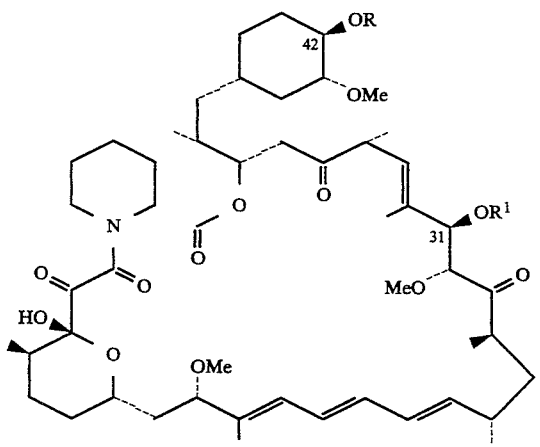

wherein R and R$^1$ are each, independently,

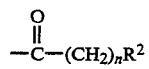

or hydrogen;

R$^2$ is a heterocyclic radical selected from the group consisting of furanyl, thiophenyl, pyrrolyl, isopyrrolyl, pyrazolyl, imidazolyl, 1,2,3-triazolyl, 1,2,4-triazolyl, 1,2-dithiolyl, 1,3-dithiolyl, 1,2,3-oxathiolyl, isoxazolyl, oxazolyl, thiazolyl, isothiazolyl, 1,2,3-oxadiazolyl, 1,2,5-oxadiazolyl, 1,3,4-oxadiazolyl, 1,2,3,4-oxatriazolyl, 1,2,3,5-oxatriazolyl, 1,2,3-dioxazolyl, 1,2,4-dioxazolyl, 1,3,2-dioxazolyl, 1,3,4-dioxazolyl, 1,2,5-oxathiazolyl, 1,3-oxathiolyl, 1,2-pyranyl, 1,4-pyranyl, pyridinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,2,6-oxazinyl, 1,4-oxazinyl, isoxazinyl, 1,2,5-oxathiazinyl, 1,4-oxazinyl, o-isoxazinyl, p-isoxazinyl, 1,2,5-oxathiazinyl, 1,2,6-oxathiazinyl, 1,3,5,2-oxadiazinyl, azepinyl, oxepinyl, thiepinyl, 1,2,4-diazepinyl, benzofuranyl, isobenzofuranyl, thionaphthenyl, indolyl, indolenyl, 2-isobenzazolyl, 1,5-pyrindinyl, pyrano[3,4-b]pyrrolyl, benzpyrazolyl, benzisoxazolyl, benzoxazolyl, anthranilyl, 1,2-benzopyranyl, quinolinyl, isoquinolinyl, tetrahydroisoquinolinyl, cinnolinyl, quinazolinyl, naphthyridinyl, pyrido[3,4-b]pyridinyl, pyrido[4,3-b]pyridinyl, pyrido[2,3-b]pyridinyl, 1,3,2-benzozazinyl, 1,4,2-benzoxazinyl, 2,3,1-benzoxazinyl, 3,1,4-benzoxazinyl, 1,2-benzisoxazinyl, 1,4-benzisoxazinyl, carbazolyl, and purinyl, which may be optionally mono-, di-, or tri-substituted with a group selected from alkyl of 1-6 carbon atoms, arylalkyl 7-10 carbon atoms, alkoxy of 1-6 carbon atoms, cyano, halo, hydroxy, nitro, carbalkoxy of 2-7 carbon atoms, trifluoromethyl, trifluoromethoxy, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —SO$_3$H, —PO$_3$H, and —CO$_2$H;

n=0-6;

with the proviso that R and R$^1$ are both not hydrogen, or a pharmaceutically acceptable salt thereof.

2. The compound of claim 1 wherein R$^1$ is hydrogen or a pharmaceutically acceptable salt thereof.

3. The compound of claim 2 wherein R$^1$ is hydrogen and n=0 or a pharmaceutically acceptable salt thereof.

4. The compound of claim 3 wherein R$^2$ is pyridinyl, pyrazinyl, triazinyl, pyrimidinyl, pyridazinyl, imidazolyl, pyrazolyl, quinolinyl, tetrahydroquinolinyl, or isoquinolinyl, or a pharmaceutically acceptable salt thereof.

5. The compound of claim 1 which is rapamycin 42-ester with 2-methylnicotinic acid or a pharmaceutically acceptable salt thereof.

6. The compound of claim 1 which is rapamycin 42-ester with nicotinic acid or a pharmaceutically acceptable salt thereof.

7. The compound of claim 1 which is rapamycin 42-ester with 6-methylpyridine-3-carboxylic acid or a pharmaceutically acceptable salt thereof.

8. The compound of claim 1 which is rapamycin 42-ester with 5-methylpyrazine-2-carboxylic acid or a pharmaceutically acceptable salt thereof.

9. The compound of claim 1 which rapamycin 42-ester with quinoline 6-carboxylic acid is or a pharmaceutically acceptable salt thereof.

10. The compound of claim 1 which is rapamycin 42-ester with quinoline-8-carboxylic acid or a pharmaceutically acceptable salt thereof.

11. The compound of claim 1 which is rapamycin 42-ester with 1-methyl-1,2,3,4-tetrahydroquinoline-6-carboxylic acid or a pharmaceutically acceptable salt thereof.

12. A method of inducing immunosuppression in a mammal in need thereof, which comprises administering an immunosuppressive effective amount of a compound of the structure

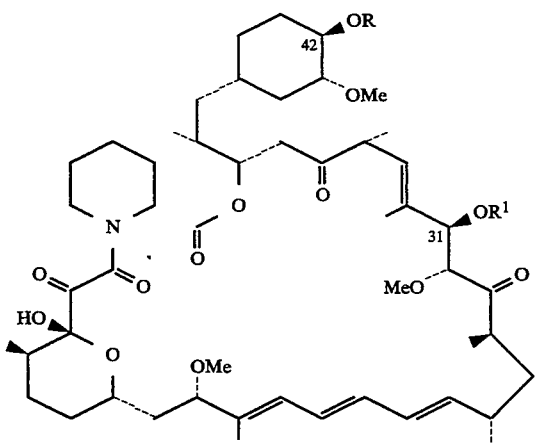

wherein R and R¹ are each independently,

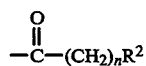

or hydrogen;

R² is a heterocyclic radical selected from the group consisting of furanyl, thiophenyl, pyrrolyl, isopyrrolyl, pyrazolyl, imidazolyl, 1,2,3-triazolyl, 1,2,4-triazolyl, 1,2-dithiolyl, 1.3-dithiolyl, 1,2,3-oxathiolyl, isoxazolyl, oxazolyl, thiazolyl, isothiazolyl, 1,2,3-oxadiazolyl, 1,2,5-oxadiazolyl, 1,3,4-oxadiazolyl, 1,2,3,4-oxatriazolyl, 1,2,3,5-oxatriazolyl, 1,2,3-oxazolyl, 1,2,4-dioxazolyl, 1,3,2-dioxazolyl, 1,3,4-dioxazolyl, 1,2,5-oxathiazolyl, 1,3-oxathiolyl, 1,2-pyranyl, 1,4-pyranyl, pyridinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,2,6-oxazinyl, 1,4-oxazinyl, isoxazinyl, 1,2,5-oxathiazinyl, 1,4-oxazinyl, o-isoxazinyl, p-isoxazinyl, 1,2,5-oxathiazinyl, 1,2,6-oxathiazinyl, 1,3,5,2-oxadiazinyl, azepinyl, oxepinyl, thiepinyl, 1,2,4-diazepinyl, benzofuranyl, isobenzofuranyl, thionaphthenyl, indolyl, indolenyl, 2-isobenzazolyl, 1,5-pyrindinyl, pyrano[3,4-b]pyrrolyl, benzpyrazolyl, benzisoxazolyl, benzoxazolyl, anthranilyl, 1,2-benzopyranyl, quinolinyl, isoquinolinyl, tetrahydroisoquinolinyl, cinnolinyl, quinazolinyl, naphthyridinyl, pyrido[3,4-b]pyridinyl, pyrido[4,3-b]pyridinyl, pyrido[2,3-b]pyridinyl, 1,3,2-benzozazinyl, 1,4,2-benzoxazinyl, 2,3,1-benzoxazinyl, 3,1,4-benzoxazinyl, 1,2-benzisoxazinyl, 1,4-benzisoxazinyl, carbazolyl, and purinyl, which may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, —PO₃H, and —CO₂H;

n=0–6;

with the proviso that R and R¹¹ are both not hydrogen, or a pharmaceutically acceptable salt thereof.

13. A method of treating transplantation rejection or graft vs. host disease in a mammal in need thereof which comprises administering an antirejection effective amount of a compound of the structure

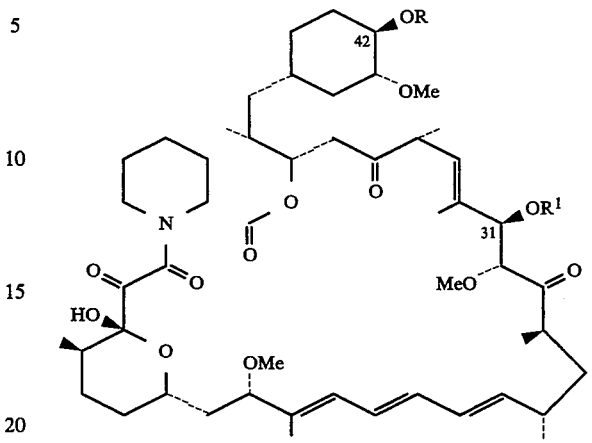

wherein R and R¹ are each, independently,

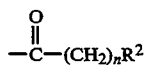

or hydrogen;

R² is a heterocyclic radical selected from the group consisting of furanyl, thiophenyl, pyrrolyl, isopyrrolyl, pyrazolyl, imidazolyl, 1,2,3-triazolyl, 1,2,4-triazolyl, 1,2-dithiolyl, 1,3-dithiolyl, 1,2,3-oxathiolyl, isoxazolyl, oxazolyl, thiazolyl, isothiazolyl, 1,2,3-oxadiazolyl, 1,2,5-oxadiazolyl, 1,3,4-oxadiazolyl, 1,2,3,4-oxatriazolyl, 1,2,3,5-oxatriazolyl, 1,2,3-dioxazolyl, 1,2,4-dioxazolyl, 1,3,2-dioxazolyl, 1,3,4-dioxazolyl, 1,2,5-oxathiazolyl, 1,3-oxathiolyl, 1,2-pyranyl, 1,4-pyranyl, pyridinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,2,6-oxazinyl, 1,4-oxazinyl, isoxazinyl, 1,2,5-oxathiazinyl, 1,4-oxazinyl, o-isoxazinyl, p-isoxazinyl, 1,2,5-oxathiazinyl, 1,2,6-oxathiazinyl, 1,3,5,2-oxadiazinyl, azepinyl, oxepinyl, thiepinyl, 1,2,4-diazepinyl, benzofuranyl, isobenzofuranyl, thionaphthenyl, indolyl, indolenyl, 2-isobenzazolyl, 1,5-pyrindinyl, pyrano[3,4-b]pyrrolyl, benzpyrazolyl, benzisoxazolyl, benzoxazolyl, anthranilyl, 1,2-benzopyranyl, quinolinyl, isoquinolinyl, tetrahydroisoquinolinyl, cinnolinyl, quinazolinyl, naphthyridinyl, pyrido[3,4-b]pyridinyl, pyrido[4,3-b]pyridinyl, pyrido[2,3-b]pyridinyl, 1,3,2-benzozazinyl, 1,4,2-benzoxazinyl, 2,3,1-benzoxazinyl, 3,1,4-benzoxazinyl, 1,2-benzisoxazinyl, 1,4-benzisoxazinyl, carbazolyl, and purinyl, which may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, —PO₃H, and —CO₂H;

n=0–6;

with the proviso that R and R¹ are both not hydrogen, or a pharmaceutically acceptable salt thereof.

14. A method of treating rheumatoid arthritis in mammal in need thereof which comprises administering an antiarthritis effective amount of a compound of the structure

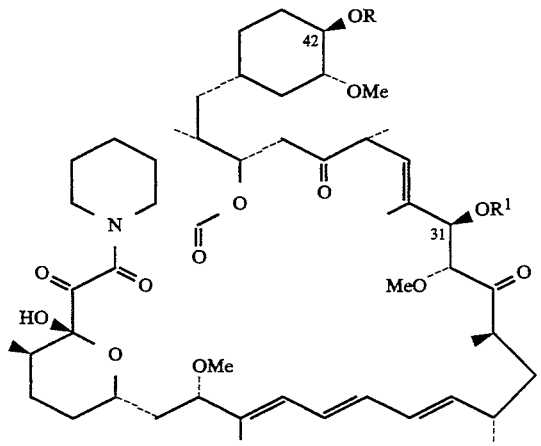

wherein R and R¹ are each, independently,

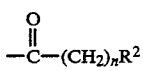

or hydrogen;
R² is a heterocyclic radical selected from the group consisting of furanyl, thiophenyl, pyrrolyl, isopyrrolyl, pyrazolyl, imidazolyl, 1,2,3-triazolyl, 1,2,4-triazolyl, 1,2-dithiolyl, 1,3-dithiolyl, 1,2,3-oxathiolyl, isoxazolyl, oxazolyl, thiazolyl, isothiazolyl, 1,2,3-oxadiazolyl, 1,2,5-oxadiazolyl, 1,3,4-oxadiazolyl, 1,2,3,4-oxatriazolyl, 1,2,3,5-oxatriazolyl, 1,2,3-dioxazolyl, 1,2,4-dioxazolyl, 1,3,2-dioxazolyl, 1,3,4-dioxazolyl, 1,2,5-oxathiazolyl, 1,3-oxathiolyl, 1,2-pyranyl, 1,4-pyranyl, pyridinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,2,6-oxazinyl, 1,4-oxazinyl, isoxazinyl, 1,2,5-oxathiazinyl, 1,4-oxazinyl, o-isoxazinyl, p-isoxazinyl, 1,2,5-oxathiazinyl, 1,2,6-oxathiazinyl, 1,3,5,2-oxadiazinyl, azepinyl, oxepinyl, thiepinyl, 1,2,4-diazepinyl, benzofuranyl, isobenzofuranyl, thionaphthenyl, indolyl, indolenyl, 2-isobenzazolyl, 1,5-pyrindinyl, pyrano[3,4-b]pyrrolyl, benzpyrazolyl, benzisoxazolyl, benzoxazolyl, anthranilyl, 1,2-benzopyranyl, quinolinyl, isoquinolinyl, tetrahydroisoquinolinyl, cinnolinyl, quinazolinyl, naphthyridinyl, pyrido[3,4-b]pyridinyl, pyrido[4,3-b]pyridinyl, pyrido[2,3-b]pyridinyl, 1,2,3-benzozazinyl, 1,4,2-benzoxazinyl, 3,2,1-benzoxazinyl, 3,1,4-benzoxazinyl, 1,2-benzisoxazinyl, 1,4-benzisoxazinyl, carbazolyl, and purinyl, which may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, —PO₃H, and —CO₂H;
n=0–6;
with the proviso that R and R¹ are both not hydrogen, or a pharmaceutically acceptable salt thereof.

15. A pharmaceutical composition which comprises a compound of the structure

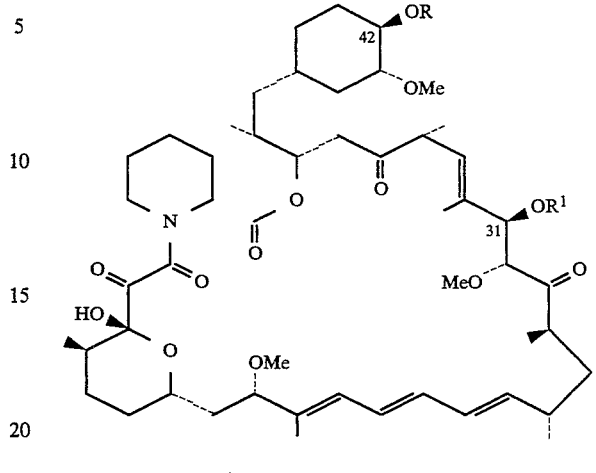

wherein R and R¹ are each, independently,

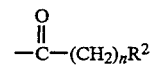

or hydrogen;
R² is a heterocyclic radical selected from the group consisting of furanyl, thiophenyl, pyrrolyl, isopyrrolyl, pyrazolyl, imidazolyl, 1,2,3-triazolyl, 1,2,4-triazolyl, 1,2-dithiolyl, 1,3-dithiolyl, 1,2,3-oxathiolyl, isoxazolyl, oxazolyl, thiazolyl, isothiazolyl, 1,2,3-oxadiazolyl, 1,2,5-oxadiazolyl, 1,3,4-oxadiazolyl, 1,2,3,4-oxatriazolyl, 1,2,3,5-oxatriazolyl, 1,2,3-dioxazolyl, 1,2,4-dioxazolyl, 1,3,2-dioxazolyl, 1,3,4-dioxazolyl, 1,2,5-oxathiazolyl, 1,3-oxathiolyl, 1,2-pyranyl, 1,4-pyranyl, pyridinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,2,6-oxazinyl, 1,4-oxazinyl, isoxazinyl, 1,2,5-oxathiazinyl, 1,4-oxazinyl, o-isoxazinyl, p-isoxazinyl, 1,2,5-oxathiazinyl, 1,2,6-oxathiazinyl, 1,3,5,2-oxadiazinyl, azepinyl, oxepinyl, thiepinyl, 1,2,4-diazepinyl, benzofuranyl, isobenzofuranyl, thionaphthenyl, indolyl, indolenyl, 2-isobenzazolyl, 1,5-pyrindinyl, pyrano[3,4-b]pyrrolyl, benzpyrazolyl, benzisoxazolyl, benzoxazolyl, anthranilyl, 1,2-benzopyranyl, quinolinyl, isoquinolinyl, tetrahydroisoquinolinyl, cinnolinyl, quinazolinyl, naphthyridinyl, pyrido[3,4-b]pyridinyl, pyrido[4,3-b]pyridinyl, pyrido[2,3-b]pyridinyl, 1,3,2-benzozazinyl, 1,4,2-benzoxazinyl, 2,3,1-benzoxazinyl, 3,1,4-benzoxazinyl, 1,2-benzisoxazinyl, 1,4-benzisoxazinyl, carbozolyl, and purinyl, which may be optionally mono-, di-, or tri-substituted with a group selected from alkyl of 1–6 carbon atoms, arylalkyl of 2–10 carbon atoms, alkoxy of 1–6 carbon atoms, cyano, halo, hydroxy, nitro, carbalkoxy of 7–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, —PO₃H, and —CO₂H;
n=0–6;
with the proviso that R and R¹ are both not hydrogen, or a pharmaceutically acceptable salt thereof, and a pharmaceutical carrier.

* * * * *